United States Patent [19]
Orvik et al.

[11] Patent Number: 5,461,153
[45] Date of Patent: Oct. 24, 1995

[54] 2-ALKOXY-4-HYDRAZINOPYRIMIDINE COMPOUNDS

[75] Inventors: Jon A. Orvik, Midland; Dawn Shiang, Sanford, both of Mich.

[73] Assignee: DowElanco, Indianapolis, Ind.

[21] Appl. No.: 148,760

[22] Filed: Nov. 5, 1993

[51] Int. Cl.⁶ .................................................. C07D 239/47
[52] U.S. Cl. ......................................................... 544/317
[58] Field of Search ............................................. 544/317

[56] References Cited

U.S. PATENT DOCUMENTS

| | | | |
|---|---|---|---|
| 4,528,288 | 7/1985 | Wade | 514/258 |
| 5,163,995 | 11/1992 | Van Heertum | 544/318 |

FOREIGN PATENT DOCUMENTS 951652  3/1964  United Kingdom .

OTHER PUBLICATIONS

Yosha et al., *Yakugaku Zasshi*, 95, 219–226 (1975) (Chem. Abs. 83,43117z (1975); both the reference and the abstract are submitted).

Naito, et al., *Chem. Pharm. Bull.*, 17, 1467–1478 (1969).

Johar, *Indian Journal of Chemistry*, 8, 759–760 (1970).

Broadbent et al., *J. Chem. Soc.*, 1965, 3369–3372.

Miller et al., *J. Chem. Soc.*, 1963, 5642–5659.

Undheim et al., *Acta Chemica Scandinavica*, 23, 294–299 (1969).

*Primary Examiner*—John M. Ford
*Attorney, Agent, or Firm*—D. Wendell Osborne

[57] ABSTRACT

5-Alkoxy-1,2,4-triazolo[4,3-c]pyrimidine-3(2H)-thione compounds, such as 5-ethoxy-8-fluoro-1,2,4-triazolo[4,3-c]pyrimidine-3(2H)-thione, were prepared by cyclization of 2-alkoxy-4-hydrazinopyrimidine compounds, such as 2-ethoxy-5-fluoro-4-hydrazinopyrimidine, with carbon disulfide and hydrogen peroxide. The reaction can be carried out in the presence of a trialkylamine, such as triethylamine, in which case a trialkylammonium salt is obtained. The products are useful intermediates in the preparation of 5-alkoxy[1,2,4]triazolo[1,5-c]pyrimidine-2-sulfonamide herbicides.

5 Claims, No Drawings

2-ALKOXY-4-HYDRAZINOPYRIMIDINE COMPOUNDS

BACKGROUND OF THE INVENTION

The present invention relates to 2-alkoxy-4-hydrazinopyrimidine compounds and to their use in the preparation of 5-alkoxy-1,2,4-triazolo[4,3-c]pyrimidine- 3(2H)-thione compounds.

5-Alkoxy[1,2,4]triazolo[1,5-c]pyrimidine-2-sulfonamide compounds that are potent herbicides are described in U.S. Pat. No. 5,163,995 and are disclosed therein to be prepared in a multistep process from appropriately substituted 2-alkylthio-4-hydrazinopyrimidine compounds. The preparation requires a cyclization with carbon disulfide, a rearrangement, and a substitution reaction wherein the alkylthio moiety is replaced with an alkoxy moiety in the presence of an ethylenically unsubstituted compound capable of reacting with and removing the displaced alkanethiol. This process is lengthy, produces the desired products in only moderate yield, and results in a by-product alkylthioethyl moiety-containing compound which must be disposed of as waste. Improved methods for preparing herbicidal 5-alkoxy[1,2,4] triazolo[1,5-c]pyrimidine-2-sulfonamide compounds, including improved methods for preparing intermediates that are useful in their preparation, would be of considerable value as would the starting materials and intermediates that would be required to implement the improved methods.

A few 2-alkoxy-4-hydrazinopyrimidine compounds are known in the art and are known to be useful as chemical intermediates (e.g., *Chem. Pharm. Bull.*, 17, 1467–78 (1969) and *J. Chem. Soc.* 1970, 2661–66). The halogenated 2-alkoxy-4-hydrazinopyrimidine compounds that would be required to produce herbicidal N-(substituted phenyl)-5-alkoxy-(7- or 8-halo)[1,2,4]triazolo[1,5-c]pyrimidine-2-sulfonamide compounds, however, have not been described.

5-Alkoxy-1,2,4-triazolo-[4,3-c]pyrimidine- 3(2H)-thione compounds have not been described in the art.

SUMMARY OF THE INVENTION

Previously unknown 2-alkoxy-(5 or 6-halo)-4-hydrazinopyrimidine compounds have now been prepared and these compounds along with other substituted 2-alkoxy-4-hydrazinopyrimidine compounds have been found to be useful in the preparation of previously unknown substituted 5-alkoxy-1,2,4-triazolo[4,3-c]pyrimidine- 3(2H)-thione compounds. The preparation of the latter has been accomplished by cyclization of the substituted 2-alkoxy-4-hydrazinopyrimidine compounds with carbon disulfide and an oxidizing agent. The 2-alkoxy-(5 or 6-halo)-4-hydrazinopyrimidine compounds and the 5-alkoxy- 1,2,4-triazolo[4,3-c]pyrimidine-3(2H)-thione compounds prepared from them were found to be useful as intermediates in the preparation of herbicidal 5-alkoxy-[1,2,4]triazolo[1,5-c] pyrimidine-2-sulfonamide compounds. The resulting process for preparing these herbicides is more economical and more readily carried out than any previously described process.

The invention includes 2-alkoxy-4-hydrazinopyrimidine compounds of Formula I:

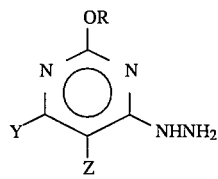

wherein

R represents $CH_3$ or $C_2H_5$ and one of Y and Z represents F, Cl, or Br and the other represents H.

Compounds of Formula I wherein one of Y and Z represents F and the other represents H are most often preferred. In other instances, such compounds wherein one of Y and Z represents Cl and the other represents H are preferred.

The invention further includes a method of use of a 2-alkoxy-4-hydrazinopyrimidine compound of the Formula I:

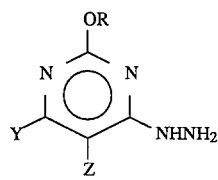

wherein one of Y and Z represents F, Cl, Br, R', or OR' and the other represents H; and R and R' each independently represents $CH_3$ or $C_2H_5$ for the preparation of a corresponding 5-alkoxy-1,2,4-triazolo[ 4,3-c]pyrimidine-3(2H)-thione compound of Formula II:

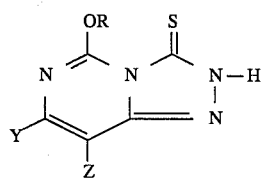

wherein R, Y, and Z are as defined hereinabove which method comprises combining said 2-alkoxy-4-hydrazinopyrimidine compound with at least about one mole of carbon disulfide and, optionally, a trialkylamine compound having a pKa of about 9.4 to about 11.4 in a suitable inert liquid medium at a temperature of about 0° C. to about 40° C. and then adding at least about one equivalent of a suitable oxidizing agent at a temperature of about 0° C. to about 40° C. to form said 5-alkoxy-1,2,4-triazolo[ 4,3-c]pyrimidine-3(2H)-thione compound or, when a trialkylamine compound is employed, a trialkylammonium salt thereof.

Trialkylamine compounds of Formula III:

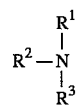

wherein $R^1$, $R^2$, and $R^3$ each independently represent $C_1$–$C_4$ alkyl or benzyl or two of $R^1$, $R^2$, and $R^3$ together represent a moiety of the formula —(CH$_2$)$_4$—, —(CH$_2$)$_5$—, O(C$_2$H$_4$—)$_2$, or CH$_3$N(C$_2$H$_4$—)$_2$ or all three of R$^1$, R$^2$, and R$^3$ together represent a moiety of the formula N(C$_2$H$_4$—)$_3$ are generally preferred when a trialkylamine compound is employed; triethylamine is usually employed. It is typically preferred to employ hydrogen peroxide as the oxidizing agent.

The trialkylammonium salt derivatives which are optionally obtained in the process are adducts of a compound of Formula II and a trialkylamine compound having a pKa of about 9.4 to about 11.4, such as those of Formula III. These salts can be acidified with an organic or inorganic acid to obtain 5-alkoxy-1,2,4-triazolo[4,3-c]pyrimidine-3(2H)-thione compounds of Formula II. The trialkylammonium salt derivatives can also be treated directly with a benzyl halide or a C$_2$–C$_4$ alkyl halide to obtain a 3-hydrocarbylthio-5-alkoxy- 1,2,4-triazolo[4,3-c]pyrimidine compound of Formula IV:

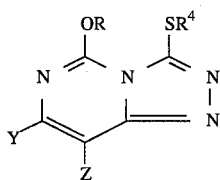

wherein R, Y, and Z are as defined hereinabove and R$^4$ represents benzyl or C$_2$–C$_4$ alkyl.

The compounds prepared by the method of use of the present invention are 5-alkoxy-1,2,4-triazolo[4,3-c]pyrimidine- 3(2H)-thione compounds of Formula II:

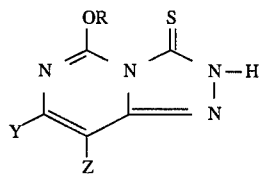

wherein
one of Y and Z represents F, Cl, Br, R', or OR' and the other represents H; and R and R' each independently represents CH$_3$ or C$_2$H$_5$ and their trialkylammonium salts, which salts are adducts of said compounds and a trialkylamine compound having a pKa of about 9.4 to about 11.4.

Compounds of Formula II wherein one of Y and Z represents F, Cl, or Br and the other represents H are generally preferred; the fluorinated compounds are usually more preferred, and the chlorinated compounds are sometimes preferred. Trialkylammonium salts that are adducts of Formula III:

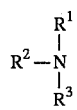

wherein R$^1$, R$^2$, and R$^3$ each independently represents C$_1$–C$_4$ alkyl or benzyl or two of R$^1$, R$^2$, and R$^3$ together represent a moiety of the formula —(CH$_2$)$_4$—, —(CH$_2$)$_5$—, O(C$_2$H$_4$—)$_2$, or CH$_3$N(C$_2$H$_4$—)$_2$ or all three of R$^1$, R$^2$, and R$^3$ together represent a moiety of the formula N(C$_2$H$_4$—)$_3$ are generally preferred salts; salts that are adducts of tri- ethylamine are more preferred.

DETAILED DESCRIPTION OF THE INVENTION

The halogenated 2-alkoxy-4-hydrazinopyrimidine compounds of the invention are compounds of Formula I:

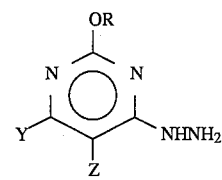

wherein R represents methyl or ethyl and one of Y and Z represents fluorine, chlorine, or bromine and the other represents hydrogen. These compounds can be described as 2-alkoxy-4-hydrazinopyrimidine compounds wherein the alkoxy moiety is methoxy or ethoxy and wherein there is a single bromine, chlorine or fluorine substituent in the 5- or 6-position. The compounds of this description are 2-ethoxy-5-(fluoro, chloro, or bromo)-4-hydrazinopyrimidine, 2-methoxy-5-(fluoro, chloro, or bromo)-4-hydrazinopyrimidine, 2-ethoxy-6-(fluoro, chloro, or bromo)-4-hydrazinopyrimidine, and 2-methoxy-6-(fluoro, chloro, or bromo)-4-hydrazinopyrimidine. The fluorinated compounds are usually preferred, but the chlorinated compounds are sometimes preferred.

In some instances Chemical Abstracts names compounds of Formula I as 6-hydrazino compounds rather than 4-hydrazino compounds. The compounds of the present invention are those of Formula I regardless of the Chemical Abstracts name, but, the compounds will be referred to herein as 4-hydrazino compounds in the general statements.

Some specifically preferred compounds include 5-fluoro-4-hydrazino-2-methoxypyrimidine, 5-chloro-4-hydrazino-2-methoxypyrimidine, 2-ethoxy-4-fluoro-6-hydrazinopyrimidine, and 4-chloro-2-ethoxy-6-hydrazinopyrimidine.

The 2-alkoxy-5-halo-4-hydrazinopyrimidine compounds of Formula I can be prepared from 2,4-dimethoxy- 5-(fluoro, chloro, or bromo)pyrimidine or 2,4-diethoxy- 5-(fluoro, chloro, or bromo)pyrimidine by treatment with hydrazine hydrate and triethylamine. Similarly, the 2-alkoxy-6-(fluoro, chloro, or bromo)-4-hydrazinopyrimidine compounds can be prepared from the corresponding 4,6-dihalo-2-methoxypyrimidine or 4,6-dihalo-2-ethoxypyrimidine compound by treatment with hydrazine hydrate and triethylamine. The reactions are best carried out in water or in a solvent, such as acetonitrile, at a temperature of between about 0° C. about 40° C. using about one mole of triethylamine and slightly in excess of one mole of hydrazine hydrate. The desired 2-alkoxy-5-halo-4-hydrazinopyrimidine and 2-alkoxy-6-halo- 4-hydrazinopyrimidine compounds of Formula I can be recovered by adding water to promote precipitation and recovering the precipitate by filtration, centrifugation, or extraction. These compounds can, however, often be employed as intermediates without recovery and/or purification. Other compounds of Formula I can be prepared analogously from starting materials known in the art.

Substituted 2-alkoxy-4-hydrazinopyrimidines of Formula I were found to be useful for the preparation of correspondingly substituted 5-alkoxy-1,2,4-triazolo[ 4,3-c]pyrimidine-3(2H)-thione compounds of Formula II:

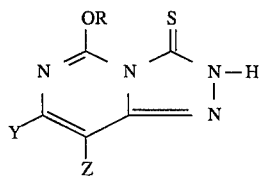

wherein R represents methyl or ethyl and one of Y and Z represents fluorine, chlorine, bromine, methyl, ethyl, methoxy, or ethoxy and the other represents hydrogen and trialkylammonium salts thereof. The trialkylammonium salts can be looked upon as adducts of a compound of Formula II and a trialkylamine compound having a pKa of about 9.4 to about 11.4, including, but not exclusively defined by, trialkylamine compounds of Formula III:

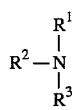

wherein $R^1$, $R^2$, and $R^3$ each independently represents alkyl of 1 to 4 carbon atoms or benzyl or two of $R^1$, $R^2$, and $R^3$ together, taken with the nitrogen atom, represent pyrrolidine, piperidine, morpholine, or N-methylpiperazine or all three of $R^1$, $R^2$, and $R^3$ together, taken with the nitrogen atom, represent 1,4-diazabicyclo [2,2,2] octane.

The process is often of special interest for the preparation of compounds of Formula II wherein one of Y and Z represents fluorine and the other represents hydrogen and their trialkylammonium salts. It is usually preferred to obtain, as a final product, a compound of Formula II. When a trialkylammonium salt derivative is obtained, it is typically preferable to obtain one wherein each of $R^1$, $R^2$, and $R^3$ of Formula III represents ethyl (the triethylammonium salt).

The compounds of Formula II are named and are depicted herein as 3(2H)-thione compounds. They could equally well have been named and depicted as 3-thiol compounds of Formula IIA since the two structures are keto-enol type isomers and are in dynamic equilibrium.

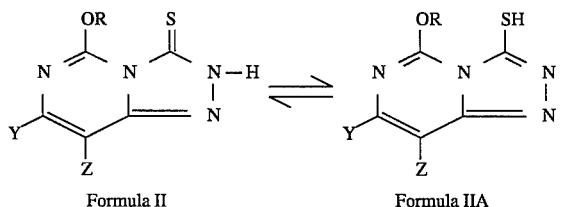

Formula II      Formula IIA

The process involved in this method of use can be conducted by combining the 2-alkoxy-4-hydrazinopyrimidine compound of Formula I wherein R represents methyl or ethyl and one of Y and Z represents fluorine, chlorine, bromine, methyl, ethyl, methoxy, or ethoxy and the other represents hydrogen with at least about one mole of carbon disulfide. These reagents can be combined in any order and can be combined either in the absence of or in the presence of a trialkylamine compound having a pKa of about 9.4 to about 11.4, such as a trialkylamine compound of Formula III wherein $R^1$, $R^2$, and $R^3$ each, independently, represents alkyl of 1 to 4 carbon atoms or benzyl or two of $R^1$, $R^2$, and $R^3$ together, taken with the nitrogen atom, represent pyrrolidine, piperidine, morpholine, or N-methylpiperazine or all three of $R^1$, $R^2$, and $R^3$ together, taken with the nitrogen atom, represent 1,4-diazabicyclo[2,2,2]octane. The reactants and optional trialkylamine compound are combined in a suitable inert liquid medium at a temperature of about 0° C. to about 40° C. Other strong bases, such as alkali metal hydroxides, alkoxides, and phenoxides can be present up to about 1 mole per mole of the compound of Formula I. If more than one mole is employed, the desired products of Formula II rearranges and cannot be recovered in good yield. After a short reaction period, an oxidizing agent such as hydrogen peroxide, is added to the mixture at a temperature of about 0° C. to about 40° C. The mixture obtained is typically agitated to assure good mixing. The reaction proceeds quickly with the formation of the desired 5-alkoxy-1,2,4-triazolo[4,3-c]pyrimidine- 3(2H)-thione compound of Formula II or, if a trialkylamine compound is employed, of a trialkylammonium salt thereof. If a different strong base is present, at least a portion of the compound of Formula II will be obtained in the form of the corresponding salt and the mixture must be acidified to recover the compound of Formula II.

It is postulated that the conversion of a compound of Formula I to a compound of Formula II takes place in three distinct chemical reaction steps. A dithiocarbazoic acid compound or a trialkylammonium salt of a dithiocarbazoic acid compound of the formula:

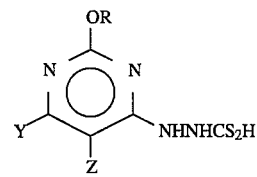

is first formed as an intermediate. The dithiocarbazoic acid compound or its salt then reacts with the oxidizing agent to form elemental sulfur and an isothiocyanate compound of the formula:

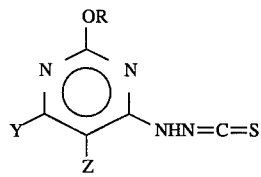

which compound cyclizes to the desired compound of Formula II. If a trialkylamine compound is present, it reacts with the compound of Formula II obtained to produce a trialkylammonium salt. If an alkali metal hydroxide or alkoxide is present, at least some of the compound of Formula II is in the form of an alkali metal salt. The operability of the claimed method of use is, however, not dependent upon the veracity of the stated postulation.

It is often preferred to carry out the method of use process without the addition of a trialkylamine compound, in which circumstance the product is a compound of Formula II. It is, however, sometimes preferred to carry out the process in the presence of at least about one molar quantity of a trialkylamine having a pKa of about 9.4 to about 11.4, such as a trialkylamine compound of Formula III, per mole of 2-alkoxy-4-hydrazinopyrimidine compound of Formula I. Triethylamine is a preferred trialkylamine. When a trialkylamine compound is employed, the trialkylammonium salt form of the compound of Formula II is generally obtained as the product. From about 1 to about 2 moles of trialkylamine are generally employed.

Any oxidizing agent capable of converting a dithiocarbamic acid compound to an isothiocyanate compound can be employed. Suitable oxidizing agents include hydrogen peroxide, halogens such as bromine, peracids such as peracetic acid, diacyl peroxides such as acetyl peroxide, alkyl peroxides such as t-butyl peroxide, and the like. Hydrogen peroxide, however, was found to be superior and is highly preferred. At least about one mole (one equivalent) of hydrogen peroxide per mole of 2-alkoxy-4-hydrazinopyrimidine compound is required and up to about 3 moles are typically employed. Larger excesses of hydrogen peroxide tend to promote the formation of by-products and should be avoided. It is generally preferred to employ from about 1 to about 2 moles and more preferred to employ from about 1.1 to about 1.5 mole.

Carbon disulfide is generally employed in an amount of at least about one mole per mole of 2-alkoxy-4-hydrazinopyrimidine compound. Typically, from about 1 to about 5 moles are employed. It is often preferred to employ from about 1 to about 3 moles and more preferred to employ from about 1.1 to about 2.0 moles.

A suitable inert liquid medium is one that does not react appreciably with the starting materials, intermediates, or products of the process and in which at least a portion of the reactants and intermediates are soluble. It is usually desirable that the solvent be miscible with water in some proportions. Suitable solvents include acetonitrile, dioxane, methanol, ethanol, 2-propanol, 1,2-dimethoxyethane, N,N-dimethylformamide, N-methyl-2-pyrrolidinone and the like, employed alone or diluted with water. Acetonitrile is often preferred and mixtures of acetonitrile and water are more preferred. Methanol and ethanol are sometimes preferred. Solvent:water ratios of about 1:10 to about 20:1 can be employed when water is used. Solvent:water ratios of about 1:3 to about 10:1 are generally preferred, and ratios of about 1:1 to about 4:1 are often more preferred. A ratio of about 2:1 is, in some circumstances, most preferred. The water can be added in conjunction with the reaction involving the carbon disulfide and/or in conjunction with the reaction involving the oxidizing agent.

The method of use process of the invention proceeds well at ambient temperatures and is generally carried out at temperatures of about 0° C. to about 40° C. Temperatures of about 20° C. to about 30° C. are often preferred. The fact that the process can be carried out at such low and convenient temperatures is an important feature of the process because carbon disulfide is an extremely flammable material.

The compounds of Formula II prepared by the process when a trialkylamine compound is not employed typically precipitate from the reaction mixture as they form. They can be recovered by adding water, if necessary to ensure complete precipitation, and recovering the solids, which are a mixture of the compound of Formula II and elemental sulfur, by filtration or centrifugation. The mixture can be dried by conventional means, including extraction with dry solvent and air drying. The sulfur and other impurities can be removed by conventional means, such as by extraction with carbon disulfide, recrystallization, liquid chromatography, and the like.

The trialkylammonium salt derivatives of the compounds of Formula II that are prepared when the process of the invention is carried out in the presence of a trialkylamine compound can be recovered by a variety of means. For example, the salts can be recovered by adding sufficient water (if necessary) to completely dissolve them, filtering to remove elemental sulfur, and then evaporating the water and solvents. Alternatively, the solvents can be removed by filtration or evaporation to obtain a mixture of the salt and elemental sulfur and the sulfur removed by extraction with carbon disulfide. The product first obtained can be purified by conventional means, such as by extraction or by recrystallization from a solvent.

It is often convenient to utilize 2-alkoxy-4-hydrazinopyrimidine compounds to prepare compounds of Formula II or the trialkylammonium salts thereof in a process that further involves their preparation. In this embodiment of the invention, a 2-alkoxy-4-hydrazinopyrimidine compound of Formula I is first prepared from an appropriate 2,4-di(methoxy or ethoxy)-5-(substituted)pyrimidine, 2-(methoxy or ethoxy)-4-halo-6-(substituted)pyrimidine compound, or other suitable 2-(methoxy or ethoxy)pyrimidine intermediate by treatment with hydrazine and a trialkylamine compound, such as a trialkylamine compound of Formula III. The reaction is generally carried out in an organic solvent, such as acetonitrile, or in a mixture of water and an organic solvent, at a temperature of between about 0° C. about 40° C. About one mole of trialkylamine and slightly in excess of one mole of hydrazine per mole of 2-(methoxy or ethoxy-)pyrimidine compounds are generally used. It is often preferred to employ a mixture of acetonitrile and water such that the products and by-products obtained remain at least partially in solution. The product mixture obtained, which contains a 2-alkoxy-4-hydrazinopyrimidine compound of Formula I, is then treated with carbon disulfide and hydrogen peroxide to obtain a 5-alkoxy-1,2,4-triazolo[4,3-c]pyrimidine-3(2H)-thione compound of Formula II without any further recovery or isolation. The reaction is carried out essentially as described hereinabove. At least about one mole of carbon disulfide and at least about one mole of oxidizing agent, preferably hydrogen peroxide, are employed and the reaction is carried out in the absence of or in the presence of a trialkylamine compound, such as those of Formula III, at a temperature of about 0° C. to about 40° C. The reaction proceeds in the same manner as the corresponding reaction starting with a 2-alkoxy-4-hydrazinopyrimidine compound of Formula I in the form of an isolated solid and the desired 5-alkoxy-1,2,4-triazolo[ 4,3-c]pyrimidine-3(2H)-thione compound of Formula II or, if a trialkylamine compound is employed, a trialkylammonium salt thereof is obtained.

It is often desirable to convert the trialkylammonium salts of the compounds of Formula II obtained when a trialkylamine compound is employed to the corresponding compounds of Formula II. This can be accomplished by the addition of an organic or inorganic acid. Essentially any acid having a pKa below about 8 can be employed; cheap and readily available acids, such as hydrochloric acid or acetic acid are typically used. The reaction is typically carried out in water or in a mixture of an organic solvent and water. The compound of Formula II generally precipitates as it forms. Additional water can be added, if necessary to ensure complete precipitation. It is often convenient to carry out the reaction in the medium in which the salt was prepared, which medium is usually preferably a mixture of acetonitrile and water. Any elemental sulfur is typically removed by filtration or extraction with carbon disulfide before acidification. The precipitated compounds of Formula II can be recovered by conventional means, such as by filtration or centrifugation, and can be dried by conventional means. They can be purified by conventional means, such as by extraction or recrystallization from a solvent.

It is sometimes desirable to convert a compound of Formula II into a trialkylammonium salt derivative. This is readily accomplished by dissolving the compound in an organic solvent, such as acetonitrile, and adding at least about one mole of a trialkylamine compound having a pKa of about 9.4 to about 11.4, such as a trialkylamine compound of Formula III. If a solvent in which the compound of Formula II is soluble but the trialkylammonium salt is insoluble is selected, the salt precipitates and can be recovered by filtration or centrifugation. The salts can be dried by conventional means. If a solvent in which the salt is soluble, such as a 1:1 mixture of acetonitrile and water, is selected, the salt remains in solution and can be utilized in that form. Trialkylammonium salt formation can, further, be employed to remove the by-product elemental sulfur from compounds of Formula II. To accomplish this, the compound of Formula II, in the form of a mixture with elemental sulfur such as that described hereinabove, is converted into a trialkylammonium salt in a reaction medium in which the latter is soluble, the resulting mixture is filtered to remove elemental sulfur, and the compound of Formula II is recovered by adding an acid.

Trialkylammonium salt derivatives of the compounds of Formula II are often employed as intermediates for further reactions, with or without recovery. These compounds are often, for example, converted to 3-hydrocarbylthio-5-alkoxy-1,2,4-triazolo[4,3-c]pyrimidine derivative compounds of Formula IV:

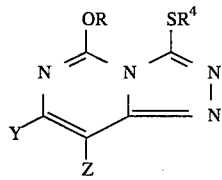

wherein R, Y, and Z are as defined hereinabove for compounds of Formula II and $R^4$ represents benzyl or 2 to 4 carbon alkyl. This is accomplished by treating the salts with a benzyl halide or a 2 to 4 carbon alkyl halide, such as benzyl chloride or ethyl bromide, or a substantially equivalent benzylating or alkylating agent under reaction conditions essentially the same as those reported for related alkylation reactions well-known to those of ordinary skill in the art. Thus, the salt and the hydrocarbyl halide are combined in a solvent in which the salt is at least partially soluble, such as acetonitrile/water, methanol, or ethanol, and the mixture is allowed to stand or is heated to from about 40° C. to about 80° C. Excessive heating and large excesses of trialkylamine compound lead to undesirable side reactions. The resulting compounds of Formula IV can be recovered by conventional means, such as by filtration or by evaporation of the solvents, and can be purified readily by conventional means, such as by liquid chromatography, recrystallization from a solvent, or extraction.

Similarly, the compounds of Formula II can be converted to compounds of Formula IV by treating them with a trialkylamine compound, such as a trialkylamine compound of Formula III, or with another weakly nucleophilic base and treating the resulting salt with a benzyl halide or a 2 to 4 carbon alkyl halide or a substantial equivalent thereof under reaction conditions essentially the same as those described hereinabove.

The 5-alkoxy-1,2,4-triazolo[4,3-c]pyrimidine-3(2H)-thione compounds of Formula II wherein R represents methyl or ethyl and one of Y and Z represents fluorine, chlorine, bromine, methyl, ethyl, methoxy, or ethoxy and the other represents hydrogen as well as the trialkylammonium salts that are adducts of the compounds of Formula II and trialkylamine compounds having a pKa of about 9.4 to about 11.4, such as the compounds of Formula III, that are prepared by the process involved in the method of use of the present invention are novel. Such compounds can be characterized as 5-alkoxy-1,2,4-triazolo[4,3-c]pyrimidine-3(2H)-thione compounds wherein the alkoxy group is methoxy or ethoxy and wherein there is a single halogen, alkyl, or alkoxy substituent in the 7- or 8-position and the reaction products of these compounds with trialkylamine compounds. 5-Alkoxy-(7- or 8-fluoro, chloro, or bromo)-1,2,4-triazolo[4,3-c]pyrimidine- 3(2H)-thione compounds are often preferred. The compounds of Formula II in this preferred class include 5-ethoxy-7-(fluoro or chloro)-1,2,4-triazolo[ 4,3-c]pyrimidine-3(2H)-thione, 5-methoxy-7-(fluoro or chloro)-1,2,4-triazolo[4,3-c]pyrimidine-3(2H)-thione, 5-ethoxy-8-(fluoro or chloro)-1,2,4-triazolo[4,3-c]pyrimidine- 3(2H)-thione, and 5-methoxy-8-(fluoro or chloro)-1,2,4-triazolo[4,3-c]pyrimidine-3(2H)-thione. The fluoro compounds are generally of the most interest, but the chloro compounds are sometimes preferred. Trialkylammonium salts derived from the trialkylamines of Formula III are preferred salts; triethylammonium salts are more preferred.

The 5-alkoxy-1,2,4-triazolo[4,3-c]pyrimidine- 3(2H)-thione compounds of Formula II are not very stable and tend to decompose on standing, even in the solid state. It is preferred to utilize these compounds as intermediates in the synthesis of other, more stable compounds soon after preparing them.

The 5-alkoxy-1,2,4-triazolo[4,3-c]pyrimidine- 3(2H)-thione compounds of Formula II prepared in the process of the invention can be converted into 5-alkoxy[ 1,2,4]triazolo[1,5-c]pyrimidine-2(3H)-thione compounds of Formula V:

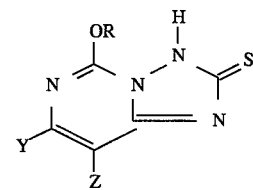

wherein R represents methyl or ethyl and one of Y and Z represents fluoro, chloro, bromo, methyl, ethyl, methoxy, or ethoxy, and the other represents hydrogen. (These compounds could alternately be depicted as and named as 5-alkoxy[1,2,4]triazolo[1,5-c]pyrimidine-2-thiol compounds). The conversion is effected by treatment of the compound of Formula IV with at least about one mole of a strong base, such as sodium ethoxide or potassium methoxide. The reaction is typically carried out in an alcohol solvent at ambient temperature with agitation to ensure mixing. When R represents methyl, the strong base is preferably sodium or potassium methoxide and the solvent is methanol; when R represents ethyl, the strong base is preferably sodium or potassium ethoxide and the solvent is ethanol. Large excesses of the strong base, high temperatures, and excessively long reaction times lead to undesirable side reactions and should be avoided.

Similarly, compounds of Formula IV can be converted into 2-hydrocarbylthio-5-alkoxy[1,2,4]triazolo[ 1,5-c]pyrimidine compounds of Formula VI:

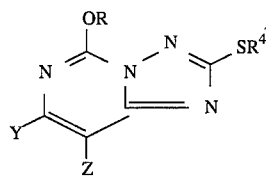

wherein R represents methyl or ethyl, one of Y and Z represents fluoro, chloro, bromo, methyl, ethyl, methoxy, or ethoxy and the other represents hydrogen, and $R^4$ represents benzyl or $C_2$–$C_4$ alkyl by treatment with a strong base, such as sodium ethoxide or potassium methoxide. The reaction is typically carried out in an alcohol solvent at ambient temperature with agitation to ensure mixing. When R represents methyl, the strong base is preferably sodium or potassium methoxide and the solvent is methanol; when R represents ethyl, the strong base is preferably sodium or potassium ethoxide and the solvent is ethanol.

The same compounds of Formula VI can be prepared from a compound of Formula V by alkylation with a benzyl halide or a $C_2$–$C_4$ alkyl halide or a substantial equivalent in the presence of a base, such as sodium ethoxide, potassium methoxide, or a trialkylamine compound, such as those of Formula III. Benzyl chloride and ethyl bromide are typical alkylating agents. The compound of Formula V, the base, and the hydrocarbyl halide are typically combined in a solvent in which salts are at least partially soluble, such as acetonitrile/water, methanol, or ethanol, and the mixture is allowed to stand or is heated to about 40° C. to about 80° C. When R represents methyl, the base is preferably sodium methoxide or a trialkylamine compound and the solvent is methanol; when R represents ethyl, the base is preferably sodium ethoxide or a trialkylamine compound and the solvent is ethanol. Excessive heating and large excesses of base lead to undesirable side reactions. The resulting compounds of Formula VI can be recovered by conventional means, such as by filtration or by evaporation of the solvents, and can be purified readily by conventional means, such as by liquid chromatography, recrystallization from a solvent, or extraction.

The compounds of Formulas V and VI are known from U.S. Pat. Nos. 5,163,995 and 5,177,206, the appropriate portions of which are hereby incorporated by reference, to be useful for the preparation of herbicidal 5-alkoxy[1,2,4]triazolo[1,5-c]pyrimidine-2-sulfonamide compounds. The compounds of Formulas V and VI are converted to the corresponding 2-chlorosulfonyl compounds by treatment with chlorine in an aqueous medium, such as aqueous chloroform, and the 2-chlorosulfonyl compounds obtained can be coupled with an appropriately substituted aniline or N-trialkylsilylaniline compound in an inert solvent, such as acetonitrile, in the presence of a tertiary amine compound and/or a catalytic amount of dimethyl sulfoxide.

The following examples are presented to illustrate the invention. They should not be construed as limitations on the claims.

EXAMPLES

1. Preparation of 5-Fluoro-4-hydrazino-2-methoxypyrimidine

5-Fluoro-2,4-dimethoxypyridine (158 g (grams), 1.00 mol), 150 g (3.00 mol) of hydrazine hydrate, and 237 g of methanol were placed in a 1 L (liter) flask and heated to reflux (about 70° C.) for 3.5 hours with stirring. The mixture, which became homogeneous and then heterogeneous again, was then cooled to 0°–5° C. and the solids present were recovered by vacuum filtration, washed with 150 mL (milliliters) of cold methanol, and dried to constant weight. The title compound, which was obtained as colorless needles melting at 188°–189° C., amounted to 151.5 g (96 percent of theory).

NMR data (DMSO-d6) δ: $^1$H: 3.77 (s, 3H), 4.38 (2H), 7.83 (d(J=3.6 Hz), 1H), 8.87 (1H); $^{13}$C: 54.2,137.9 (d($J_{CF}$=19.6 Hz)), 141.5 (d($J_{CF}$=244.8 Hz)), 154.3 (d($J_{CF}$=13.7 Hz)), 160.6.

2. Preparation of 2-Ethoxy-4-fluoro-6-hydrazinopyrimidine

A mixture of 100 g of 94 percent purity (0.59 mol) 2-ethoxy-4,6-difluoropyrimidine, 275 mL of acetonitrile, and 107 g of water was prepared and cooled to 10° C. To this was added 68 g (0.67 mol) of triethylamine and then 34 g (0.68 mol) of hydrazine hydrate, slowly with stirring and cooling (at 5° to 10° C.). When all of the hydrazine had been added, the mixture was stirred another 15 min with cooling and was then allowed to warm. After a total of 1 hour, the solids that formed were recovered by vacuum filtration and were washed twice with 100 mL portions of water and then with 50 mL of ethanol. The title compound, which was obtained as a white solid melting at 141°–143° C., amounted to 79.7 g {80 percent of theory).

Elemental Analysis for $C_6H_9FN_4O$: Calc.: %C, 41.9; %H, 5.27; %N, 32.5 Found: %C, 42.2; %H, 5.12; %N, 32.6

Alternately, 2-ethoxy-4,6-difluoropyrimidine (16.0 g, 100 mmol), water (100 mL) and triethylamine (11.1 g, 110 mmol) were combined in a reaction vessel and the mixture was stirred under nitrogen and cooled to 0° C. by means of an ice bath. A solution of hydrazine hydrate (5.00 g, 100 mmol) in 20 mL of water was added over a 25 min. period with stirring and cooling. After all of the hydrazine hydrate had been added, the mixture was stirred until the reaction was complete. The reaction mixture became a thick slurry due to the formation of a precipitate. The precipitate was recovered by vacuum filtration and was washed with cold water and dried under reduced pressure at 40° C. to obtain 16.0 g of the title compound (93 percent of theory) as a white solid.

3. Preparation of 4-Chloro-2-ethoxy-6-hydrazinopyrimidine

A mixture of 50.0 g of 95 percent purity (0.246 mol) 4,6-dichloro-2-ethoxypyrimidine, 26.9 g (0.266 mol) of triethylamine, 200 mL of ethanol, and 200 g of water was prepared and cooled to 5° C. To this was added 13.4 g (0.266 mol) of hydrazine hydrate over a 15-min period with stirring and cooling at about 5° C. The mixture was stirred and allowed to warm to ambient temperature overnight. It became very thick, but approximately 10 percent of the starting material remained. Another 1.3 g (0.026 mol) of hydrazine hydrate was added and stirring was continued for another 4 hours. The solids that formed were recovered by vacuum filtration and were washed twice with 100 mL portions of water and then with 100 mL of acetonitrile. The title compound, which was obtained as a white powder melting at 170°–173° C., amounted to 43.9 g (88 percent of theory).

Elemental Analysis for $C_6H_9ClN_4O$: Calc.: %C, 38.2; %H, 4.81; %N, 29.7 Found: %C, 38.5; %H, 4.74; %N, 29.6

4. Preparation of 5-Chloro-4-hydrazino-2-methoxypyrimidine

A solution containing 0.35 g (2.0 mmol) of 5-chloro-2, 4-dimethoxypyrimidine and 0.35 g (7.0 mmol) of hydrazine hydrate in 2.9 g of methanol was heated at reflux with stirring for 8 hours. The mixture was then cooled causing a precipitate to form. Water was added until the precipitation appeared to be complete and the precipitate was then recovered by vacuum filtration and allowed to air dry overnight to obtain 0.23 g (66 percent of theory) of the title compound as a white solid. The product melted at 172°–173° C. after changing crystalline form from needles to cube-like shapes in a phenomenon that appeared to involve sublimation.

NMR data (DMSO-d6) δ: $^1$H: 3.85 (s, 3H), 4.50 (2H), 7.97 (s, 1H), 8.7 (1H); $^{13}$C: 54.17, 105.40, 152.77, 159.39, and 163.39.

A 91 percent yield of 97 percent purity product was obtained when a 15:1 mole ratio of hydrazine to 5-chloro-2,4-dimethoxypyrimidine and a 5 hour reaction period were employed and the temperature was held at 50°–60° C.

5. Preparation of 8-Fluoro-5-methoxy-1,2,4-triazolo[4,3-C]pyrimidine-3(2H)-thione 5-Fluoro-4-hydrazino-2-methoxypyrimidine (15.81 g, 0.100 mol), 47 g of methanol, 10.2 g (0.100 mol) of triethylamine, and 11.4 g (0.15 mol) of carbon disulfide were combined in a 250 mL flask under nitrogen at ambient temperature with stirring to obtain a yellow, heterogeneous mixture. The mixture was cooled to 15° C. with an ice bath. Hydrogen peroxide (12.5 g of 30 percent aqueous, 0.11 mol) was then added by means of a syringe pump, the syringe of which was inserted into the flask through a septum. The addition was made over a 1-hour period with stirring and cooling to maintain the temperature at about 15° C. The mixture was allowed to react and warm for 1 hour and the resulting heterogeneous orange mixture was vacuum filtered to remove the solid sulfur. The filtrate was cooled in an ice bath and acidified with 17.6 mL (0.11 mol) of 6.25N hydrochloric acid diluted with 125 mL of water. The resulting precipitate was recovered by vacuum filtration and dried under reduced pressure to obtain 18.81 g (94 percent of theory) of the title compound as an off-white solid melting at 166° C. with decomposition.

NMR data (DMSO-d6) δ: $^1$H: 4.01 (s, 3H), 7.64 (d(J=2.8 Hz), 1H), 14.5 (brs, 1H); $^{13}$C: 56.00, 125.6 (d($J_{CF}$=22.0 Hz)), 141.6, 141.7 (d($J_{CF}$=41.7 Hz)), 146.0 (d($J_{CF}$=191.0 Hz)), and 161.2.

6. Preparation of 5-Ethoxy-7-fluoro-1,2,4-triazolo[4,3-c]pyrimidine-3(2H)-thione Procedure A: A mixture containing approximately 5.2 g (30 mmol) of 2-ethoxy-4-fluoro-6-hydrazinopyrimidine in a solvent composed of 50 mL of acetonitrile and 15 mL of water was prepared and to this was added 6.4 mL (107 mmol) of carbon disulfide at ambient temperature with stirring. The heterogeneous white mixture became a pale yellow solution after about 10 min and then 3.8 mL of 30 percent aqueous hydrogen peroxide (37 mmol) and 3.2 mL of water were added over a 30-min period with stirring and cooling to hold the temperature at about 25° C. The mixture was allowed to react another 10 min and then 3.22 g (32 mmol) of triethylamine was added and the resulting mixture was filtered to remove sulfur. The filtrate was acidified with 10 mL of 3.75N hydrochloric acid (38 mmol) and the resulting mixture was filtered to recover the precipitate that formed. This was washed with water and dried to obtain 4.4 g (66 percent of theory) of the title compound of 97 percent purity as a light beige solid melting at 170° C. Considerable product remained in the filtrate.

Elemental Analysis for $C_7H_7FN_4OS$: Calc.: %C, 39.2; %H, 3.29; %N, 26.2 Found: %C, 39.3; %H, 3.07; %N, 25.9

Procedure B: A mixture containing 32.6 g (0.186 mol) of 2-ethoxy-4-fluoro-6-hydrazinopyrimidine and 21.1 g (0.277 mol) of carbon disulfide in a solvent composed of 83.7 mL of acetonitrile and 33.3 mL of water was prepared under nitrogen in a 500 mL flask equipped with a condensor and an opening covered by a septum through which the syringe of a syringe pump was inserted. The mixture was allowed to react with stirring at ambient temperature for 15 min and then 22.2 g of 30 percent aqueous hydrogen peroxide (0.196 mol) was added over a 1-hour period by means of the syringe with stirring and cooling to hold the temperature at about 25° C. The mixture was allowed to react for another hour and then was cooled to about 0° C. The precipitated product and sulfur by-product were recovered by vacuum filtration and washed with 150 mL of water, 150 mL of a 1:1 mixture of water and acetonitrile, and finally with two 75 mL portions of acetonitrile and were then air dried to obtain 45.1 g of a light beige product that was 74.8 percent the title compound (85 percent of theory yield), 13.9 percent sulfur, and 0.5 percent water.

7. Preparation of 5-Ethoxy-7-fluoro-1,2,4-triazolo[4,3-c]pyrimidine-3(2H)-thione from 2-Ethoxy-4,6-difluoropyrimidine A mixture consisting of 1.42 parts of acetonitrile, 2.66 parts of water, and 1.60 parts of 2-ethoxy- 4,6-difluoropyrimidine is prepared and cooled to 5° C. Hydrazine hydrate (0.526 parts) and 1.06 parts of triethylamine are added with cooling and stirring under nitrogen at a rate such that the temperature does not rise above 10° C. When the addition is complete, the mixture is allowed to warm to ambient temperature and stir until the reaction is complete. Carbon disulfide (1.14 parts) is then added with stirring and the mixture is allowed to react for 15 min. Hydrogen peroxide as a 30 percent solution in water (1.20 parts) is then added with stirring and cooling to maintain the temperature between 25° and 30° C. and the mixture is allowed to react for an additional hour at 25° C. The mixture is cooled to 0° C. and filtered in a reduced pressure apparatus to recover the insoluble material. This material is washed sequentially with 3.20 parts of water and 4.00 parts of cold acetonitrile to obtain the title compound mixed with by-product sulfur and containing up to 2 percent water and some acetonitrile.

8. Preparation of 7-Chloro-5-ethoxy-1,2,4-triazolo[4,3-c]pyrimidine-3(2H)-thione A mixture containing 20 g of 93 percent purity (99 mmol) 4-chloro-2-ethoxy-6-hydrazinopyrimidine in a solvent composed of 90 mL of acetonitrile and 26 mL of water was prepared under nitrogen in a 500 mL flask equipped with a condensor and an opening covered by a septum through which the syringe of a syringe pump was inserted. To this was added 11.3 g (148 mmol) of carbon disulfide and, after a 15-min reaction period, 16.7 g of 30 percent aqueous hydrogen peroxide (147 mmol) was added over a 15-min period by means of the syringe with stirring and cooling to hold the temperature at about 25° C. The mixture was allowed to react for another 4 hours and then was cooled to about 0° C. The precipitated product and sulfur by-product were recovered by vacuum filtration and washed with water, a 1:1 mixture of water and acetonitrile, and finally acetonitrile. The wet cake was slurried in 1 L of water at 70° C. and about 600 mL of acetonitrile was added to dissolve the solid. The resulting mixture was gravity filtered and the filtrate was allowed to cool over the weekend. The mixture was further cooled in a refrigerator and the crystals that formed were recovered by vacuum filtration, washed with acetonitrile, and dried to constant weight to obtain 14.1 g (62 percent of theory) of the title compound as an amber solid which decomposed on heating above 187° C.

Elemental Analysis for $C_7H_7ClN_4OS$: Calc.: %C, 36.4; %H, 3.06; %N, 24.3 Found: %C, 36.4; %H, 2.79; %N, 24.1

9. Preparation of 8-Chloro-5-methoxy-1,2,4-triazolo [4,3-c]pyrimidine-3(2H)-thione 5-Chloro-4-hydrazino-2-methoxypyrimidine (17.45 g, 0.10 mol) and 25 g (0.033 mol) of carbon disulfide were combined in 120 mL of acetonitrile and 30 mL of water at ambient temperature with stirring and 11.4 g (0.10 mol) of 30 percent hydrogen peroxide was added to the resulting mixture with stirring over a 2-hour period. The temperature rose from 20° C. to 48° C. Analysis of the mixture by high pressure liquid chromatography (HPLC) indicated that the reaction was complete. A 79.8 g (47.2 percent of the total) portion of the reaction mixture was diluted with 50 mL of water and the mixture was acidified with hydrochloric acid. The solids present were then recovered by vacuum filtration and dried to obtain 10.15 g of a mixture of the title compound and sulfur. The sulfur was then removed by extracting the solids with 45 g of carbon disulfide to obtain 8.08 g (80 percent of theory) of the title compound as a tan powder. This material was 92 percent pure by HPLC analysis; it decomposed on heating.

NMR data (DMSO-d6) δ: $^1$H: 4.04 (s, 3H), 7.67 (s, 1H), 14.25 (brs, 1H); $^{13}$C: 56.18, 110.08, 140.46, 145.76, 150.11, and 161.32.

10. Preparation of 3-Benzylthio-8-fluoro-5-methoxy-1,2,4-triazolo[4,3-c]pyrimidine and 2-Benzylthio-8-fluoro-5-methoxy[1,2,4]triazolo[1,5-c]pyrimidine 5-Fluoro-4-hydrazino-2-methoxypyrimidine (29.7 g, 0.188 mol), 100 g of methanol, 19.2 g (0.188 mol) of triethylamine, and 28.9 g (0.38 mol) of carbon disulfide were combined in a 500 mL flask under nitrogen at ambient temperature. Hydrogen peroxide (27 g of 30 percent aqueous, 0.24 mol) was then added by means of a syringe pump, the syringe of which was inserted into the flask through a septum, with cooling to maintain the temperature at 17° to 22° C. and with stirring. The addition was made over a 1.6-hour period. The mixture was allowed to react for another 1.5 hour and the resulting heterogeneous orange mixture was vacuum filtered to remove the solid sulfur. The solids were washed with 100 g of methanol and the filtrate (including the wash methanol), which contained the triethylammonium salt of 8-fluoro-5-methoxy-1,2,4-triazolo[4,3-c]pyrimidine- 3(2H)-thione, was transferred to a reaction flask. Benzyl chloride (24.1 g, 0.19 mol) was added at 21° C. with stirring. There was a mild exotherm which increased the temperature to 27° C. and, after about 30 min, a precipitate began to form. After 1 hour, 130 g of methanol was removed by distillation under about 600 Pascals pressure and the heterogeneous residue was subsequently cooled to about 5° C. and vacuum filtered to recover the insoluble solids. About 25 g of methanol was used to aid in the transfer of the mixture and to wash the precipitate. The wet cake obtained amounted to 55.8 g and contained approximately 42 g (0.14 mol, approximately 95 percent of theory) of 3-benzylthio-8-fluoro- 5-methoxy-1,2,4-triazolo[4,3-c]pyrimidine-3(2H)-thione.

NMR data (CDCl$_3$) δ: $^1$H: 4.11 (s, 3H), 4.61 (s, 2H), 7.3 (m, 4H), and 7.4 (m, 2H); $^{13}$C: 36.7, 56.5, 123.3, 123.6, 127.8, 128.6, 129.3, 135.9, 142.3, 144.2, 144.5, 145.7, 145.8, and 146.2.

The wet cake from above was diluted with 125 g of methanol and 2.9 g (0.013 mol) of 25 percent by weight sodium methoxide in methanol was added with stirring at ambient temperature in several portions. The mixture thickened. After 1.5 hour a solution of 2.4 mL (0.15 mol) of 6.25N aqueous hydrochloric acid in 125 mL of water was added with stirring and cooling by means of an ice bath. The mixture was cooled to about 5° C., diluted with 80 g of water, vacuum filtered to recover the insoluble solids, and dried under reduced pressure to obtain 40.3 g (95 percent of theory) of the title [1,5-c] compound as a colorless solid. This compound was identical spectroscopically and chromatographically with the compound reported in U.S. Pat. No. 5,163,995.

NMR data (DMSO-d6) δ: $^1$H: 4.17 (s, 3H), 4.51 (s, 2H), 7.3 (m, 3H), 7.45 (d(J=7.2 Hz), 2H), and 8.13(d(J=4.0Hz), 1H); $^{13}$C: 34.8, 56.4, 127.3,128.4, 128.6, 128.8, 136.7, 1.4, 144.7, 145.4, 147.1, 147.5, and 161.6.

11. Preparation of 8-Fluoro-5-methoxy[1,2,4]triazolo [1,5-c]pyrimidine-2(3H)-thione A mixture of 10.01 g (0.050 mol) of 8-fluoro- 5-methoxy-1,2,4-triazolo[4,3-c]pyrimidine-3(2H)-thione in 8.6 g of methanol was prepared and cooled with an ice water bath. Sodium methoxide in methanol (32.4 g of 25 percent, 0.15 mol) was added under nitrogen with stirring and cooling. After 2.5 hours, 25.6 mL of ice cold 6.25N aqueous hydrochloric acid was added with stirring to the thick slurry obtained. The resulting mixture was diluted with a little water and the solids were recovered by vacuum filtration and dried under reduced pressure to obtain 8.26 g (83 percent of theory) of the title compound as a colorless powder. The compound melts at 155°–160° C. and then resolidifies and does not remelt up to 230° C.

NMR data (CD$_3$CN) δ: $^1$H: 2.5–3.5 (br s, 1H), 4.21 (s, 3H), 7.92 (d(J=2.1 Hz), 1H); $^{13}$C: 57.4, 118.2, 129.2, 129.5, 143.0, 146.4, 146.7, 148.7, 149.1, and 163.8.

12. Preparation of 5-Ethoxy-7-fluoro[1,2,4]triazolo [1,5-c]pyrimidine-2 (3H) -thione A mixture of 5.8 g (26 mmol) of 5-ethoxy- 7-fluoro-1,2, 4-triazolo[4,3-c]pyrimidine-3(2H)-thione in 50 mL of absolute ethanol was prepared and to this was added at 0° C. with vigorous stirring and cooling 12.2 mL (33 mmol) of 21 weight percent sodium ethoxide in ethanol. A mildly exothermic reaction took place and the mixture changed from a suspension to a plum colored solution. The mixture was stirred at below 10° C. for 2.25 hours to complete the reaction. It was then acidified with 25 mL of 1.25N hydrochloric acid, stirred at −10° C. for 30 min, and filtered to recover the precipitate that formed. The precipitate was washed with 10 mL of cold water and dried to obtain 3.3 g (60 percent of theory) of the title compound of 98 percent purity. A second crop amounting to 1.7 g of 60 percent purity material (19 percent of theory) was obtained from the filtrate. The title compound melts at 83.5° C. to 86.5° C. and is a white solid.

NMR data (CDCl$_3$) δ: $^1$H: 1.58 (t, 3H), 4.52 (s, 2H), 4.75 (q, 2H), 7.28 (m, 3H), 7.45 (d, 2H).

The identity of the compound was further demonstrated by converting it into 2-benzylthio-5-ethoxy-7-fluoro[1,2,4] triazolo[1,5-c]pyrimidine, melting at 78°–82° C., by treatment with benzyl chloride.

13. Preparation of 8-Chloro-5-methoxy[1,2,4]triazolo [1,5-c]pyrimidine-2(3H)-thione 8-Chloro-5-methoxy-1,2,4-triazolo[4,3-c]pyrimidine-3(2H)-thione (0.215 g, 1.00 mmol) was mixed with 2.0 g of dry methanol and to this mixture was added, in increments with stirring at ambient temperature, 0.26 g (1.2 mmol) of commercial 25 percent sodium methoxide in methanol. After a 35-min reaction period, the mixture was acidified with aqueous hydrochloric acid and diluted with water. The precipitate that formed was recovered by filtration and dried to obtain 0.168 g of the title compound in 97 percent purity as determined by HPLC (76 percent of theory) as a cream colored solid. The compound can be recrystallized from a mixture of methanol and water; it decomposes, but does not melt up to 250° C.

NMR data (CDCl$_3$) δ: $^1$H: 4.28 (s, 3H), 7.93 (s, 1H), and over 14 (not observed); $^{13}$C: 56.0, 112.0, 142.1, 148.0, 153.5, and 163.0.

The identity of the product was further demonstrated by converting it into 2-benzylthio-8-chloro-5-methoxy[1,2,4] triazolo[1,5-c]pyrimidine, a compound known in U.S. Pat. No. 5,163,995, by treatment with benzyl chloride.

14. Preparation of 2,2'-Dithiobis(8-fluoro-5-methoxy [1,2,4]triazolo[1,5-c]pyrimidine).

A heterogeneous mixture composed of 76.0 g (0.380 mol) of 8-fluoro-5-methoxy[1,2,4]triazolo[1,5-c]pyrimidine-2(3H)-thione and 400 g of methanol at 24° C. was prepared and 45.3 g (0.400 mol) of ice cold 30 percent by weight hydrogen peroxide solution was added with stirring. An exothermic reaction took place raising the temperature to 43° C. The mixture was allowed to react for about 75 min and then another 13.0 g (0.115 mol) of ice cold 30 percent by weight hydrogen peroxide solution was added with stirring. The mixture was allowed to react for another 30 min and then the solids present were recovered by vacuum filtration. These solids were dried and were then slurried with methanol. The slurry was heated to reflux, cooled to 35°–45° C., and filtered to recover the insoluble solids. The solids were dried under reduced pressure at 40° C. to obtain 61.9 g of the title compound (80 percent of theory) as an off-white solid. The compound is a white powder melting at 201°– 208° C. (dec.).

NMR data (DMSO-d6) δ: $^1$H: 4.16 (s, 3H), 8.21 (d(J=2.1 Hz), 1H).

15. Preparation of 2,2'-Dithiobis(5-ethoxy-7-fluoro [1,2,4]triazolo[1,5-c]pyrimidine)

A solution of 2.9 g (13.5 mmol) of 5-ethoxy- 7-fluoro[1, 2,4]triazolo[1,5-c]pyrimidine-2(3H)-thione in 30 mL of acetonitrile was prepared and 0.80 mL (7.8 mmol) of 30 percent hydrogen peroxide was added at ambient temperature with stirring under nitrogen. The temperature rose from 21° to 34° C. The mixture was allowed to react for about 1 hour and then 15 mL of water was added and the mixture was cooled to –5° C. The precipitate that formed was recovered by vacuum filtration, washed with two 10 mL portions of a 1:1 mixture of water and acetonitrile at 5° C., and dried to obtain 2.7 g (93 percent of theory) of the title compound as a light beige powder melting at 215°–216° C.

Elemental Analysis for C$_{14}$H$_{12}$F$_2$N$_8$O$_2$S$_2$: Calc.: %C, 39.4; %H, 2.83; %N, 26.3 Found: %C, 39.6; %H, 2.75; %N, 25.9.

16. Preparation Of 2,2'-Dithiobis(5-ethoxy-7-fluoro [1,2,4]triazolo[1,5-c]pyrimidine) From 4,6-Difluoro-2-ethoxypyrimidine A mixture consisting of 32.7 g (0,202 mol) of 2-ethoxy-4,6-difluoroethoxypyrimidine, 59 g of acetonitrile, and 36 g of water was prepared in a reaction vessel and the mixture was stirred under nitrogen and cooled to about 5° C. To this was added 21.3 g (0.208 mol) of triethylamine and then 10.6 g (0,208 mol) of hydrazine monohydrate with stirring and cooling at a rate that maintained the reaction temperature at less than 15° C. After all of the hydrazine monohydrate had been added and the exotherm had subsided, the mixture was allowed to warm to ambient temperature to complete the reaction. A solution containing about 32.7 g (0.202 mol) of 2-ethoxy-4-fluoro-6-hydrazinopyrimidine in approximately 95 g of aqueous acetonitrile was obtained.

The solution of 2-ethoxy-4-fluoro-6-hydrazinopyrimidine in aqueous acetonitrile obtained above was placed into a reaction vessel and 23.1 g (0.303 mol) of carbon disulfide was added with stirring under nitrogen. After about 15 min, 23.8 g (0.210 mol) of 30 percent by weight aqueous hydrogen peroxide was added with stirring and cooling to hold the temperature at about 25°–30° C. A precipitate formed. The mixture was allowed to react for about 1 hour and was then cooled to 0° C. It was then filtered to recover the precipitate. The precipitate was washed first with two 75 mL portions of cold water to remove impurities and then with two 50 mL portions of cold acetonitrile to remove water. The 48.7 g of solid material obtained was determined to be 71 percent 5-ethoxy-7-fluoro-1,2,4-triazolo[4,3-c]pyrimidine-3(2H)-thione by HPLC (35 g, 80 percent of theory) and to contain less than 2 percent water by Karl Fischer titration. Elemental sulfur by-product was the major contaminant.

The 48.7 g (0.16 mol) of 5-ethoxy-7-fluoro- 1,2,4-triazolo [4,3-c]pyrimidine-3(2H)-thione as a 71 percent mixture with sulfur and acetonitrile obtained above was combined with 150 g of dry ethanol and the mixture was cooled to about 0° C. To this was added 67.7 g (0.21 mol) of 21 percent sodium ethoxide in ethanol with cooling and stirring such that the temperature was maintained between 5° and 15° C. The pH of the mixture was about 12. The mixture was filtered to remove the solid, insoluble sulfur and it was washed with 20 g of dry ethanol. The filtrate (including the wash ethanol) was allowed to react at about 7° C. for about another 2 hours and then 21.7 g (0.22 mol) of concentrated hydrochloric acid was added to obtain 5-ethoxy-7-fluoro[1,2,4]triazolo[1,5-c]pyrimidine-2(3H)-thione as a thin slurry of a light beige solid in ethanol.

The mixture of 5-ethoxy-7-fluoro[1,2,4]triazolo[1,5-c] pyrimidine-2(3H)-thione in ethanol obtained above was treated with 22.6 g (0.199 mol) of 30 percent hydrogen peroxide with stirring at ambient temperature. There was a mild exotherm. After a 40 min reaction period, the resulting mixture was filtered to recover the precipitate. This was washed with two 100 mL portions of ethanol and two 100 mL portions of water and dried at 37° C. under reduced pressure to obtain 30.9 g (65 percent of theory from 2-ethoxy-4,6-difluoropyrimidine) of the title compound as a light tan solid of 90 percent purity.

17. Preparation of 2-Chlorosulfonyl-5-ethoxy-7-fluoro [1,2,4]triazolo[1,5-c]pyrimidine from 2,2'-Dithiobis(5-ethoxy-7-fluoro[1,2,4]triazolo[1,5-c]pyrimidine)

A mixture containing 53.3 g of 88 percent purity (0.11 mol) of 2,2'-dithiobis(5-ethoxy-7-fluoro[ 1,2,4]triazolo[1,5-c]pyrimidine), 483 g of dichloromethane, and 12.0 g of water was prepared and cooled to about 5° C. Chlorine (42.5 g, 0.60 mol) was sparged into this mixture with cooling and stirring over a 2.5-hour period so that the temperature did not rise above about 15° C. Another 37.1 g of water was added during the course of the chlorine addition. The solids originally present became thicker at first and then essentially everything went into solution. The resulting mixture was diluted with about 200 mL of water and the phases were separated. The gold colored organic phase was washed with three 400 mL portions of water, dried over magnesium sulfate, filtered, and concentrated by evaporation under reduced pressure with a bath temperature up to 38° C. The title compound was contained in the residue, which amounted to 59.5 g (96 percent of theory) and was a waxy yellow-gold solid. A 12.66 g portion of this was purified by dissolving it in about 30 mL of dichloromethane, adding about 30 mL of hexane, and cooling. The precipitate that formed was recovered by filtration, dried to obtain 8.15 g of the title compound as a white solid. A 3.16 g second crop was also obtained. The product was identified spectroscopically to be the same compound as that reported in U.S. Pat. No. 5,163,995.

18. Preparation of 2-Chlorosulfonyl-5-ethoxy-7-fluoro [1,2,4]triazolo[1,5-c]pyrimidine from 5-Ethoxy-7-fluoro [1,2,4]triazolo[1,5-c]pyrimidine-2(3H)-thione A mixture consisting of 3.7 g (17.3 mmol) of 5-ethoxy-7-fluoro[1,2,4]triazolo[1,5-c]pyrimidine-2(3H)-thione, 45 mL of dichloromethane, and 15 mL of water was placed in a three necked flask equipped with a mechanical stirrer, an outlet tube connected to a caustic scrubber, a chlorine inlet sparge tube, and a cooling bath. Compete solution was not attained. Chlorine was sparged into the solution at 0° C. with stirring and cooling until 7.0 g, (99 mmol) was added. The solids all dissolved. The aqueous and organic layers were separated and the organic layer was dried over magnesium sulfate and concentrated by evaporation under reduced pressure to obtain the title compound as a residue. The recovered product, which was an orange solid of approximately 88 percent purity, amounted to 3.6 g (75 percent of theory). The compound was identified spectroscopically to be the same as that reported in U.S. Pat. No. 5,163,995.

What is claimed is:

1. A 2-alkoxy-4-hydrazinopyrimidine compound of the formula:

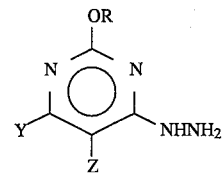

wherein

R represents $CH_3$ or $C_2H_5$ and one of Y and Z represents F, Cl, or Br and the other represents H.

2. A compound according to claim 1 wherein one of Y and Z represents F or Cl and the other represents H.

3. A compound according to claim 2 which is 2-ethoxy-4-fluoro-6-hydrazinopyrimidine.

4. A compound according to claim 2 which is 5-fluoro-4-hydrazino-2-methoxypyrimidine.

5. A compound according to claim 2 which is 5-chloro-4-hydrazino-2-methoxypyrimidine.

* * * * *